(12) United States Patent
Enomoto

(10) Patent No.: US 8,084,744 B2
(45) Date of Patent: Dec. 27, 2011

(54) RADIOGRAPHIC IMAGING SYSTEM

(75) Inventor: Jun Enomoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 189 days.

(21) Appl. No.: 12/458,013

(22) Filed: Jun. 29, 2009

(65) Prior Publication Data

US 2010/0006767 A1 Jan. 14, 2010

(30) Foreign Application Priority Data

Jul. 11, 2008 (JP) ................................. 2008-181061

(51) Int. Cl.
*H01L 27/146* (2006.01)
*G01N 23/04* (2006.01)
(52) U.S. Cl. ..................................... 250/370.09; 378/62
(58) Field of Classification Search ............. 250/370.09, 250/363.07, 363.02; 378/62, 98.8, 98.12
See application file for complete search history.

(56) References Cited

U.S. PATENT DOCUMENTS

| | | | | |
|---|---|---|---|---|
| 5,974,113 A * | 10/1999 | Bruijns et al. | ............... | 378/98.7 |
| 7,142,632 B2 | 11/2006 | Atzinger et al. | | |
| 7,626,172 B2 * | 12/2009 | Takahashi et al. | ........ | 250/363.07 |
| 7,742,570 B2 * | 6/2010 | Yamaguchi | ................ | 378/98.12 |
| 2004/0247081 A1 | 12/2004 | Halsmer et al. | | |
| 2007/0291900 A1 * | 12/2007 | Hahm et al. | ................. | 378/98.8 |
| 2008/0217535 A1 * | 9/2008 | Sato et al. | ..................... | 250/310 |

FOREIGN PATENT DOCUMENTS

| | | |
|---|---|---|
| JP | 2004-358254 | 12/2004 |
| JP | 2005-270277 | 10/2005 |
| JP | 2006-500126 | 1/2006 |

* cited by examiner

*Primary Examiner* — David Porta
*Assistant Examiner* — Faye Boosalis
(74) *Attorney, Agent, or Firm* — Jean C. Edwards, Esq.; Edwards Neils PLLC

(57) ABSTRACT

A radiographic imaging system comprises: imaging unit including a radiation source for emitting radiation and a radiation detector for detecting radiation emitted from the radiation source and having penetrated a subject; moving unit for moving the imaging unit between a plurality of imaging positions that partially share an imaging region with each other; control unit for sequentially moving the imaging unit to the imaging positions with the moving unit, causing the radiation source to emit radiation to acquire a short image with the radiation detector in each imaging position, and acquiring a dark image with the radiation detector after acquiring the short image; and image processing unit for performing residual image correction upon the short image acquired in each of the imaging positions based upon the dark image acquired immediately before the acquisition of the short image and thereafter combining corrected short images to obtain a long radiographic image.

6 Claims, 4 Drawing Sheets

RADIOGRAPHIC IMAGING SYSTEM

CROSS-REFERENCE TO RELATED APPLICATIONS

The present application claims priority from Japanese Patent Application No. 2008-181061, filed Jul. 11, 2008, the contents of which are herein incorporated by reference in their entirety.

BACKGROUND OF THE INVENTION

The present invention relates to a radiographic imaging system whereby a subject is irradiated with radiation and whereby the radiation that has penetrated the subject is detected and converted into an electric signal by a radiation detector to produce a radiographic image based upon the obtained electric signal. The present invention relates in particular to a radiographic imaging system whereby an image of an imaging region longer than the imaging surface of the radiation detector is produced.

Radiographic imaging systems are used in a variety of fields such as medicine where they are used to produce diagnostic images for medical use and industries where they are used to conduct nondestructive tests. Presently, some radiographic imaging systems use a flat panel detector (FPD) that converts radiation into an electric signal as a radiation detector for detecting the radiation that has penetrated a subject (e.g., X-ray, alpha ray, beta ray, gamma ray, electron beam, and ultraviolet ray).

In a radiographic imaging system using an FPD, a subject is irradiated with radiation emitted from a radiation source, whereupon the FPD converts the radiation that has penetrated the subject into an electric signal and reads out an electric signal corresponding to image data of the subject to produce a radiographic image.

Presently, a typical FPD has a size of only about 43 cm×43 cm. Thus, it is impossible to take a radiographic image of a long region such as the whole region of a spine (the whole spine) and the whole region of lower extremities (the whole lower extremities) of a subject (examinee).

To take a radiographic image of such a long region, radiographic imaging systems using an FPD moves the FPD in the body axis direction while effecting a plurality of exposures, i.e., taking a plurality of short images to achieve imaging of a long region, as described in JP 2004-358254 A, JP 2005-270277 A, and JP 2006-500126 A, which is referred to as long region imaging.

Specifically, when producing a long image, the number of times images are taken and the positions in which images are taken are determined according to the imaging region to be covered and the size of the FPD used, and the FPD and the radiation exposure field are moved in the body axis direction according to the determined imaging positions to take short images in different regions a plurality of times (a predetermined number of times images are to be taken), thereby producing an image of a long region covering the whole spine or the whole lower extremities. In long region imaging, short radiographic images thus taken are combined to obtain a long radiographic image of the whole spine or the whole lower extremities.

In a radiographic imaging system using the FPD, a part of the electric charge corresponding to the image data remains in the FPD even after an electric signal corresponding to the image data has been read from the FPD. When another image is taken with the remaining electric charge, the remaining electric charge inside the FPD is superimposed upon the next radiographic image as residual image, resulting in a radiographic image affected by the residual image.

Such a residual image decreases with time. Accordingly, in a case of normal imaging where an image of a whole region of the subject is taken by a single exposure, effects of a residual image does not pose a problem since a sufficient time interval is provided between an imaging and a subsequent imaging.

In long region imaging, however, about two to five images are taken successively at very short intervals as compared with normal imaging in such a manner that a short image is taken, followed by displacement of the FPD, again a next short image is taken, followed by displacement of the FPD, repeating this process. Accordingly, the residual image of the previous short image has not decreased sufficiently when the next short image is taken. This causes a problem that a short image is affected by the residual image of the previous short image, precluding a proper diagnosis.

SUMMARY OF THE INVENTION

An object of the present invention is to solve the above problems associated with the prior art and to provide a radiographic imaging system capable of preventing a residual image remaining from the previous image in the long region imaging performed by a radiographic imaging system using a radiation detector, where images are taken successively in different imaging regions, from affecting the image subsequently taken, making it possible to produce a long radiographic image free from effects of such a residual image and permitting a proper diagnosis.

A radiographic imaging system according to the invention comprising:

imaging means including a radiation source for emitting radiation and a radiation detector for detecting radiation emitted from the radiation source and having penetrated a subject;

moving means for moving the imaging means between a plurality of imaging positions that partially share an imaging region with each other;

control means for sequentially moving the imaging means to the imaging positions with the moving means, causing the radiation source to emit radiation to acquire a short image with the radiation detector in each of the imaging positions, and acquiring a dark image with the radiation detector after acquiring the short image without emitting radiation from the radiation source; and image processing means for performing residual image correction upon the short image acquired in each of the imaging positions based upon the dark image acquired immediately before the acquisition of the short image and thereafter combining corrected short images to obtain a long radiographic image.

DETAILED DESCRIPTION OF THE INVENTION

Figure 1:
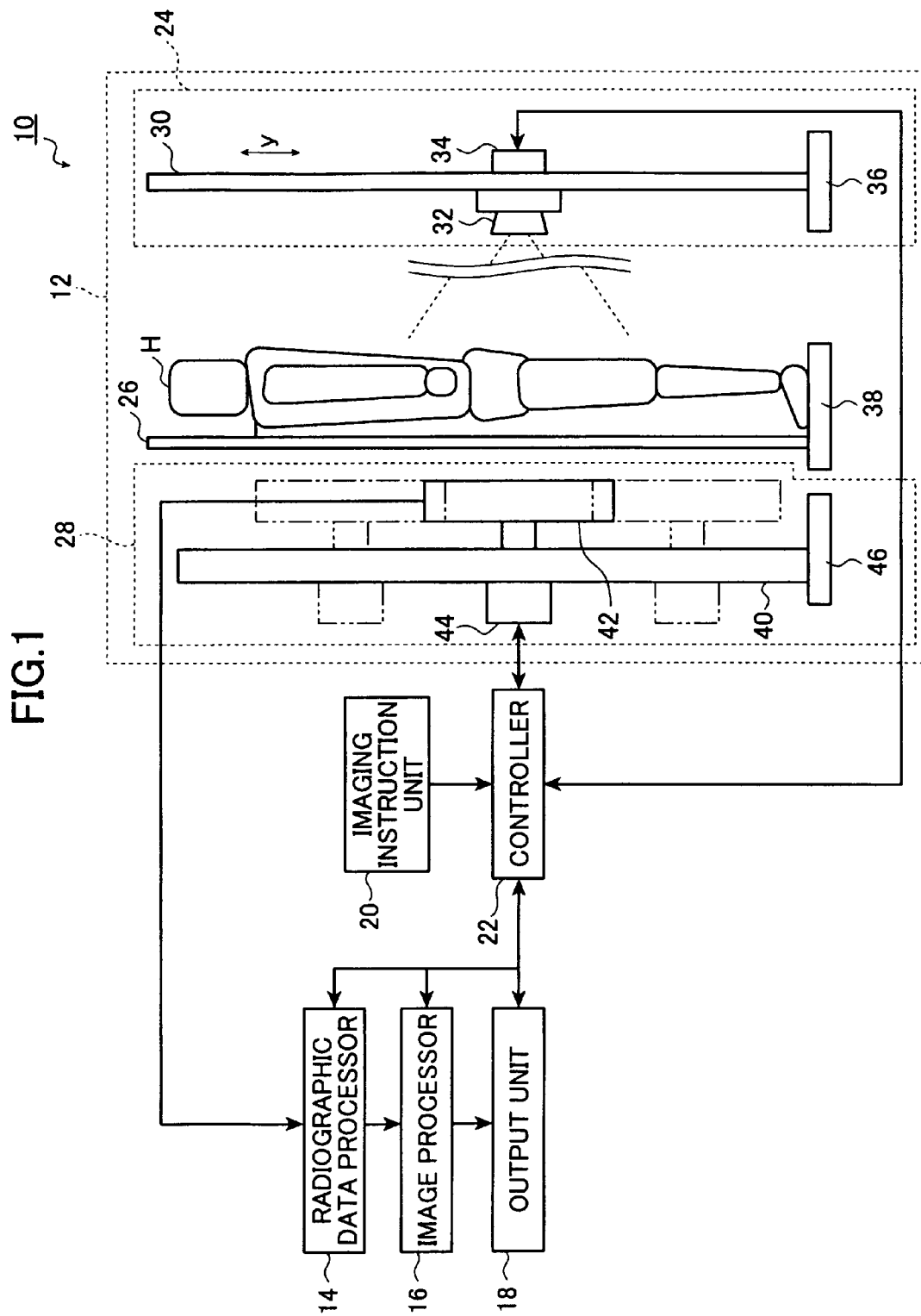
FIG. 1 is a block diagram illustrating a conceptual configuration of the radiographic imaging system according to an embodiment of the invention.

FIG. 1 is a block diagram representing a conceptual configuration of the radiographic imaging system according to an embodiment of the invention.

A radiographic imaging system (hereinafter referred to also as imaging system) 10 irradiates an examinee (subject) H with radiation, and uses a radiation detector 42 having an imaging surface to detect and convert the radiation that has penetrated the examinee H into an electric signal corresponding to image data thereby to produce a radiographic image of the examinee H based upon the electric signal obtained by conversion.

The imaging system 10 comprises an imaging unit 12, a radiographic data processor 14, an image processor 16, an output unit 18, an imaging instruction unit 20, and a controller 22.

The imaging system 10 operates in three imaging modes: a manual mode wherein imaging conditions such as radiation intensity and irradiation time (amount of radiation) are set manually; an automatic mode wherein imaging conditions such as radiation intensity and irradiation time are preset preliminarily; and a long image mode for producing a long image. The manual mode and the automatic mode are used to perform normal imaging wherein imaging of a whole region of an examinee is completed by a single exposure.

The imaging surface of the radiation detector 42 typically has a size of only about 43 cm×43 cm and, as such, does not permit taking a long radiographic image covering a whole imaging region of an examinee such as the whole region of a spine (the whole spine) and the whole region of lower extremities (the whole lower extremities) by a single exposure.

Long region imaging is a method of imaging whereby the radiation detector is moved along the examinee H's body axis (longitudinal direction) to successively perform exposure a plurality of times to take a radiographic image of such a whole region of an examinee.

Specifically, the number of times images are taken and the positions in which images are taken are determined according to the imaging region (examinee H) and the size of the imaging surface of the radiation detector 42, whereupon the radiation detector 42, i.e., the radiation exposure field, is moved according to the determined imaging positions along the examinee H's body axis to successively effect exposure (imaging) a plurality of times. A radiographic image (long image) of a long region such as the whole spine or the whole lower extremities is obtained by combining a plurality of radiographic images (short images) thus obtained.

In this embodiment, a case will be described wherein a long image mode (long region imaging) is set.

The imaging unit 12 comprises an irradiation unit 24 for irradiating the examinee H with radiation, an upright stand 26 for locating the examinee H in a given upright position for imaging, a base 38 for supporting the upright stand 26, and a radiation detection unit 28 for detecting the radiation that has penetrated the examinee H.

In the imaging unit 12, the irradiation unit 24 emits radiation toward the examinee H standing on the base 38 opposite the upright stand 26, and the radiation detection unit 28 detects and converts the radiation that has penetrated the examinee H into an electric signal (radiographic image data) to output data (analog data) of a radiographic image (short image) representing the examinee H.

The irradiation unit 24 comprises a guide rail 30, a radiation source 32, an exposure field changer 34, and a base 36 for supporting the guide rail 30.

The guide rail 30 is disposed so as to extend parallel to the upright stand 26 and hence in the vertical direction (y direction) along the examinee. The guide rail 30 supports the radiation source 32 and the exposure field changer 34 so that they can move in the vertical direction.

The radiation source 32 may be any of various radiation emission mechanisms used as radiation source in radiographic imaging systems.

The exposure field changer 34 can freely move the radiation source 32 along the guide rail 30 and places the radiation exposure field in a desired position along the examinee H's body axis (in the vertical direction).

The exposure field changer 34 may move the radiation source 32 by any moving means used in radiographic imaging systems that perform long region imaging.

Examples of such moving means include a gear transmission mechanism as exemplified by a rack and pinion, a screw transmission mechanism, a ball screw transmission mechanism, a wrapping drive mechanism using pulleys, etc., or means using a cylinder such as an air cylinder or an oil cylinder.

The upright stand 26 is a radiotransparent plate member kept upright by the base 38.

The upright stand 26 is disposed such that the plane thereof facing the radiation source 32 is parallel to an image reception plane of the radiation detector 42 described later and parallel to the moving direction (vertical direction) of the radiation source 32 and the radiation detector 42. The upright stand 26 is provided to locate the examinee H in position (imaging position along the optical axis).

The base 38 is provided to support the upright stand 26 and also serves as a footing for the examinee H to place his/her feet thereon and face the upright stand 26 for imaging.

The radiation detection unit 28 comprises a detector support stand 40, a radiation detector 42, a detector moving mechanism 44, and a base 46 for supporting the detector support stand 40. The radiation detection unit 28 acquires a dark image and the like for performing residual image correction on a radiographic image (short image) of the examinee H.

The detector support stand 40 locates the radiation detector 42 opposite the radiation source 32 (examinee H) and parallel to the moving direction (vertical direction) of the radiation source 32 and the radiation detector 42.

The radiation detector (FPD) 42 detects and converts the radiation that has penetrated the examinee H into an electric signal to output radiographic image data (analog data) representing the examinee H. The FPD 42 may be a known FPD, which, specifically, may be a direct type FPD whereby radiation is directly converted into an electric charge or an indirect type FPD whereby radiation is temporarily converted into light, which is then converted into an electric signal.

The direct type FPD is configured, for example, of a photoconductive film such as one made of amorphous selenium, a capacitor, a TFT (thin-film transistor) as a switching device, and the like. Upon entry of radiation such as X-ray in the photoconductive film, for example, electron-hole pairs are emitted from the photoconductive film. The electron-hole pairs are stored in the capacitor, and the electric charge stored in the capacitor is read out through the TFT as an electric signal.

The indirect type FPD is configured of a scintillator layer formed of a phosphor, a photodiode, a capacitor, a TFT, and other components. The scintillator layer is formed of a phosphor such as "CsI:Tl" that emits light or fluoresces in response to incident light such as radiation. The light produced by the scintillator layer in response to incoming radiation undergoes photoelectric conversion through the photodiode to produce an electric charge, which is stored in the capacitor, and the electric charge stored in the capacitor is read out through the TFT as an electric signal.

The detector moving mechanism 44 freely moves the FPD 42 in the vertical direction as illustrated by a chain double-dashed line in FIG. 1.

Figure 2:
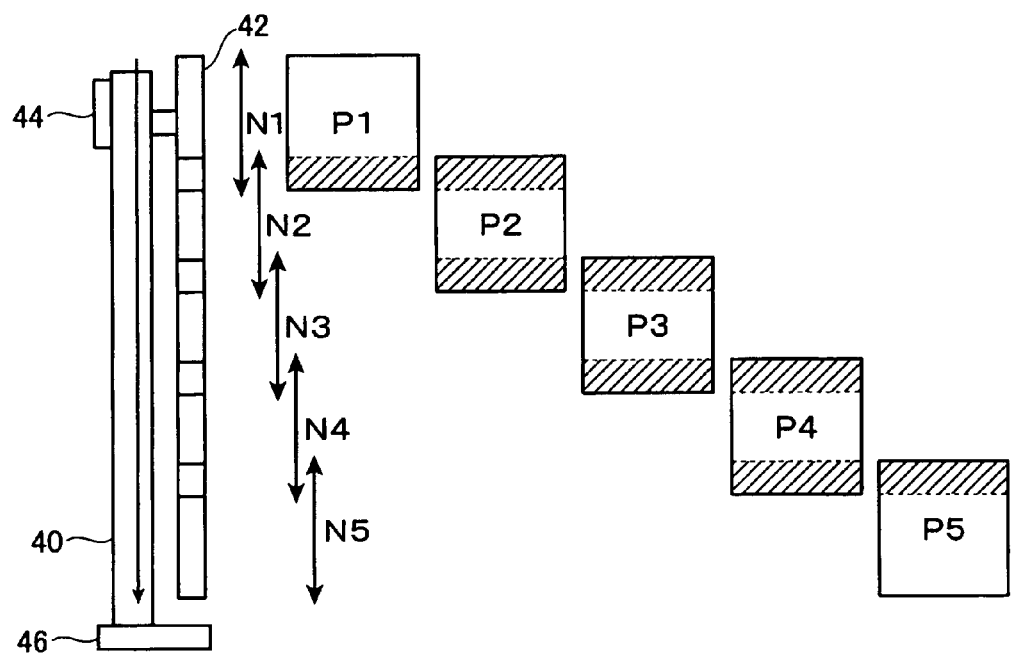
FIG. 2 is a schematic view for explaining an example of cases where long region imaging is performed according to the invention.

As schematically illustrated in FIG. 2, the FPD 42 is moved intermittently by the detector moving mechanism 44 from a higher position downwardly so as to sequentially stop at imaging positions indicated by N1, N2, N3, N4, and N5, respectively, whereas the radiation source 32 is also intermittently moved by the exposure field changer 34 in synchronism with the FPD 42.

Five short images P1 to P5 are sequentially taken by exposing the examinee H in the individual imaging positions N1 to N5 when the FPD 42 and the radiation source 32 are stationary between intermittent movement intervals.

Thus, such a manner of imaging permits producing radiographic images covering a long region of the examinee H from the imaging positions N1 to N5. A radiologist may select imaging positions as desired according to the imaging region of the examinee H to be covered by imaging like, for example, N1 and N2, N3 to N5, or N1 to N5, as well as the number of times short images are taken (number of times exposure is effected).

After taking a short image of the examinee H in an imaging position, a dark image for producing residual image correction data is acquired during a time interval during which the FPD 42 is moved to the next imaging position, for example when the FPD 42 is moved from the imaging position N1 to N2. Acquisition of the dark image will be described later in detail.

Because the imaging positions N1 to N5 share overlaps with adjacent imaging positions, short images P1 to P5 also share overlaps as illustrated in FIG. 2 (shaded areas in the drawing). The overlaps are used as margin for connecting the short images P1 to P5.

Like the exposure field changer 34 described earlier, the exposure field changer 44 may move the FPD 42 by any moving means as appropriate and by any moving means used in radiographic imaging systems to perform long region imaging.

Examples of such moving means include a gear transmission mechanism as exemplified by a rack and pinion, a screw transmission mechanism, a ball screw transmission mechanism, a wrapping drive mechanism using pulleys, etc., or means using a cylinder such as an air cylinder or an oil cylinder.

Although in FIG. 2, a maximum of five short images can be taken, the present invention is not limited this way. A maximum possible number of short images may be, for example, two to four, or six or more.

The short images are taken sequentially from a higher position (N1) downwards (toward N5) but the invention is not limited this way. Short images may be taken sequentially from a lower position (N5) upwards (toward N1).

The radiographic data processor 14 reads out a radiographic image (analog data) according to an accumulation time, in which the FPD 42 of the imaging unit 12 converts the radiation into an electric charge and accumulates the electric charge, and performs given data processing such as A/D (analog-to-digital) conversion on the read-out image data thereby to output digital data.

The radiographic data processor 14 reads out a radiographic image from the FPD 42 when a given accumulation time has passed from the time an image of the examinee H is taken (from when the examinee H is exposed to radiation). Then, when a given accumulation time has passed after reading out from the FPD 42 a radiographic image resulting from that imaging, the radiographic data processor 14 reads out a dark image that is used for residual image correction from the FPD 42.

Referring to FIG. 2, for example, the radiographic data processor 14 reads out dark image data from the FPD 42 while the FPD 42 is being moved to the imaging position N2 after the short image P1 is taken in the imaging position N1.

With such a scheme, deterioration of image quality due to residual image remaining from a short image can be prevented by using acquired dark image data even where a plurality of short images are taken in a short period of time. As a result, a long image having a high image quality can be obtained.

There is no specific limitation to the timing at which a dark image is read out while the FPD 42 is being moved. The dark image may be read out in a time period from when the FPD 42 is being moved to and including the time when it is stationary. When considering the image quality resulting from attenuation of the residual image and the processing efficiency, the dark image is preferably read out at a timing as close as possible to the time when the FPD 42 stops without timewise affecting the processing to follow. In order to reduce the amount of residual image, idle readout of a radiographic image (residual image) is preferably done at given accumulation time intervals during a time period from when radiographic image data is read out until the time when dark image data is read out.

Further, such data as offset data for offset correction may be read out in addition to radiographic image (short image) data and dark image data.

Figure 3:
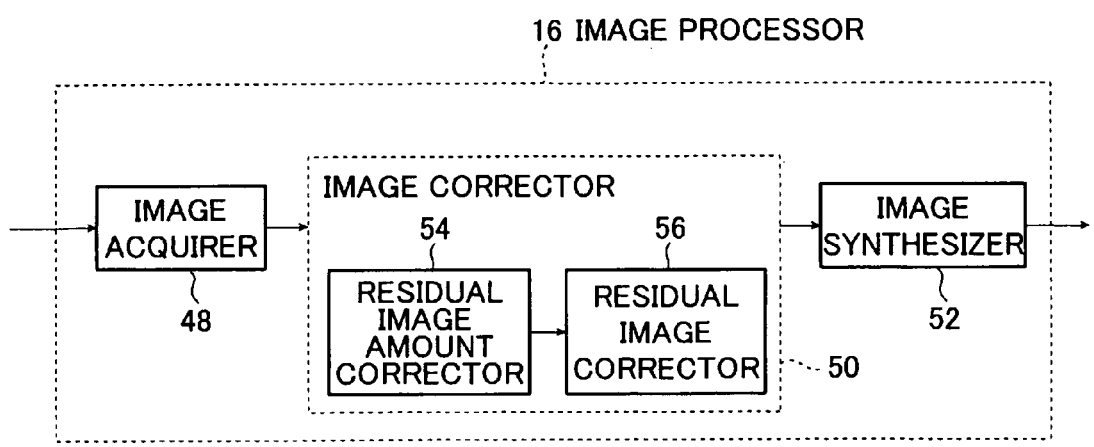
FIG. 3 is a block diagram representing a configuration of an image processor of the radiographic imaging system illustrated in FIG. 1.

The image processor 16 comprises an image acquirer 48, an image corrector 50, and an image synthesizer 52 as illustrated in FIG. 3 and performs image processing such as image correction and image synthesis on image data that is acquired from the radiographic data processor 14.

The image processor 16 comprises programs (software) that run in a computer or dedicated hardware.

The image acquirer 48 acquires radiographic image data and dark image data from the radiographic data processor 14 and supplies such data to the image corrector 50.

The image acquirer 48 may acquire various image data such as offset image data for offset correction, periodically or as required, from the radiographic data processor 14 and supply such data to the image corrector 50.

The image corrector 50 uses dark image data to perform residual image correction on a radiographic image to prevent image quality deterioration due to a residual image from the previous radiographic imaging. The image corrector 50 comprises a residual image amount corrector 54 and a residual image corrector 56.

The image acquirer 48 supplies dark image data to the residual image amount corrector 54 and radiographic image data to the residual image corrector 56, respectively.

The image corrector 50 may perform various image processing such as offset correction and sharpness processing on radiographic image data using offset image data. Radiographic image data supplied to the residual image corrector 56 may be image data subjected to image processing such as offset correction.

The residual image amount corrector 54 performs residual image amount correction on dark image data supplied from the image acquirer 48 to produce residual image data for residual image correction.

Figure 4:
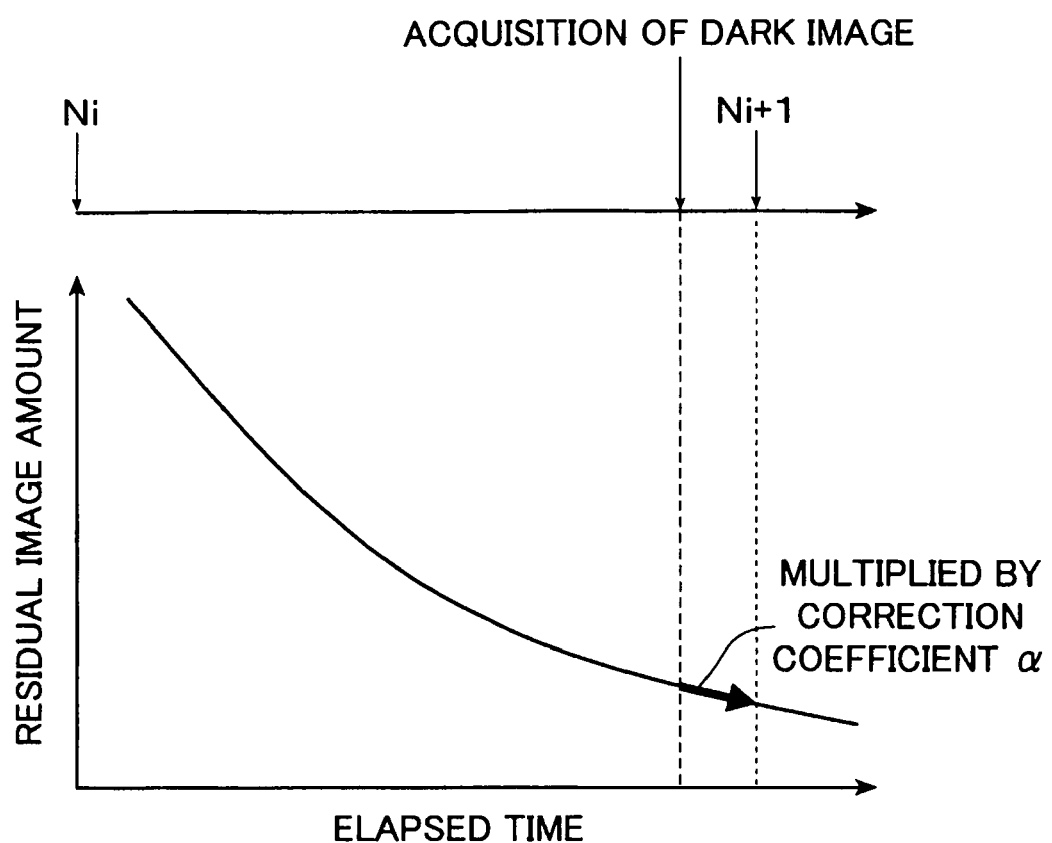
FIG. 4 is a graph illustrating a relationship between the time elapsed from when an image is taken and the amount of residual image.

FIG. 4 is a graph illustrating a relationship between the time elapsed from when an image is taken in the imaging position Ni (i=1 to 4) and the amount of residual image remaining from a radiographic image Pi taken in the imaging position Ni. As shown in the graph, the amount of residual image remaining from the radiographic image Pi obtained in the imaging position Ni decreases with time.

The residual image amount corrector 54 performs residual image amount correction by multiplying dark image data read out by the image acquirer 48 from the FPD 42 by a correction coefficient α (a constant not greater than 1, e.g., 0.9) and produces residual image data for residual image correction such that the residual image amount in hand corresponds to a residual image amount that is to be read out in the next imaging.

The correction coefficient α is a value determined individually for each FPD 42 used and is calculated preliminarily. Dark image data is preferably read out from the FPD 42 at a timing as close as possible to the timing at which an image is taken in the next imaging position Ni+1 because the change in residual image grows smaller as the readout timing comes closer to the next imaging timing, and thus the image correction accuracy can be improved.

The correction coefficient α may be calculated, for example, as follows.

A given dose of radiation is emitted, for example, and a radiographic image is read out from the FPD at given time intervals to acquire a residual image amount and obtain a graph as illustrated in FIG. 4 representing a relationship between residual image amount and elapsed time. Suppose that the curve in the graph can be expressed by a function $\exp(-t/\tau)$, where t is time and τ is a time constant, the correction coefficient α can be calculated based upon the timing at which dark image data is read out and the timing of the next imaging. The coefficient α is preliminarily calculated prior to actual use, for example, in inspection made before shipping, or in calibration.

With such residual image amount correction, the accuracy of the residual image correction can be kept from decreasing as the amount of residual image decreases from when dark image data of the radiographic image Pi is read out until the time when an image is taken in the next imaging position Ni+1.

The residual image corrector 56 subtracts residual image data supplied from the residual image amount corrector 54 from the data of the radiographic image Pi+1 taken in the imaging position Ni+1 to perform residual image correction and acquires a corrected short image P'i+1.

Although the residual image corrector 56 thus performs residual image correction on the radiographic images P2 to P5 and acquires corrected short images P'2 to P'5, the radiographic image P1 taken in the first imaging position N1 is not corrected, and the radiographic image P1 left uncorrected is used as corrected short image P'1. This is because when the radiographic image P1 is taken, more than a given time period has elapsed from the time when the previous image is taken as in normal imaging and, therefore, a residual image causes no problem in most cases.

Thus, no dark image need be acquired prior to taking the radiographic image P1, and an operation that would otherwise be required for residual image correction need not be performed. Elimination of such an operation in turn obviates the need of some processing and computation, permitting improvement on efficiency in long region imaging.

The invention is not limited thereto, however. Dark image data may be acquired before taking the first radiographic image P1, and residual image correction may be performed.

Alternatively, residual image correction on the radiographic image P1 may be performed using preliminarily acquired dark image data without acquiring dark image data before taking the radiographic image P1.

Further, a radiologist (a medical doctor) who performs imaging may be allowed to choose as desired from two or more alternatives out of the options i) no residual image correction, ii) residual image correction done without acquisition of dark image, and iii) residual image correction done with acquisition of dark image.

Alternatively, one from two or more alternatives out of the above options i), ii) and iii) may be automatically selected according to the dose of exposure effected when the previous radiographic image is taken and the time elapsed from when the previous radiographic image is taken.

Further, the radiologist may be allowed to choose between the manual selection and the automatic selection in the above residual image correction.

The residual image correction of, for example, the radiographic image P2 in the image corrector 50 are performed following the steps 1 and 2 below.

In the description to follow, X data (x, y) is data of the radiographic image P2 of an examinee taken by irradiation (image data to be corrected), Lag data (x, y) is dark image data read out from the FPD 42 without irradiation immediately before taking an image in the imaging position N2, i.e., residual image data of the radiographic image P1 taken in the imaging position N1, and α is a correction coefficient for correcting the decrease in residual image amount (amount of electric charge of residual image) occurring in a time interval from when dark image data is read out to the time when the next image is taken.

Step 1:

As expressed in the following equation (1), image data for residual image correction, Data 1 (x, y) is obtained by residual image correction achieved by multiplying the dark image data Lag data (x, y) by the residual image amount correction coefficient α. This processing is performed by the residual image amount corrector 54.

$$\text{Data 1}(x,y)=\alpha \times \text{Lag data }(x,y) \quad (1)$$

Step 2:

As expressed in the following equation (2), image data Data 2 (x, y) is obtained through residual image correction achieved by subtracting the residual image data Data 1 (x, y) from the image data X data (x, y) to be corrected. This processing is performed by the residual image corrector 56.

$$\text{Data 2}(x,y)=X\text{ data }(x,y)-\text{Data 1}(x,y) \quad (2)$$

Because residual image data contains much noise component, the subtraction in the residual image correction may partially increase the noise component of the residual image-corrected image data Data 2 (x, y).

Therefore, it is preferable that median-processed residual image data median (Data 1(x, y)) is subtracted from the image data X data (x, y) to work out residual image-corrected image data Data 2'(x, y) as shown in the equation (3) below.

$$\text{Data 2'}(x,y)=X\text{ data }(x,y)-\text{median (Data 1}(x,y)) \quad (3)$$

Note that the residual image amount correction is not essential. In other words, the dark image itself may be used as residual image data for residual image correction to perform residual image correction by following only the step 2 above. However, the residual image amount correction increases the accuracy of the residual image amount (residual image amount correction data). Thus, the residual image amount correction is desirable to increase the accuracy of the residual image correction.

In the present invention, the residual image correction may be performed by any of known methods as well as the above method.

Examples of such methods include, for example, a method whereby the accumulation time of the dark image is set to a shorter period than the accumulation time of the radiographic image to perform residual image correction using a dark image of which the accumulation time has been corrected and a method whereby an area containing a residual image is determined in residual image data to perform residual image correction solely on the area containing the residual image.

Besides these methods, one may use other methods of residual image correction described in various literature as well, examples of which include JP3540021 B, JP2000-214297 A, and JP11-500949 A.

Then, the image synthesizer 52 combines corrected short images P'1 to P'5 supplied from the residual image corrector 56 to produce and output synthetic radiographic image data of the examinee H to the output unit 18.

The corrected short images P'1 to P'5 may be combined by any method without specific limitations including any of known image synthesis methods.

Since the positions of the FPD 42 in which short images are taken, i.e., the imaging positions (coordinate positions), are known, one may, for example, use a method using the overlaps (shaded areas in FIG. 2) shared by short images derived from such coordinate positions to connect and combine the short images.

One may alternatively use a method whereby image characteristics amounts of the respective overlaps are calculated to determine the portions of the short images sharing the same image characteristics amounts as edge portions of the images, and the overlaps (shaded areas in FIG. 2) shared by short images that are derived from the edge portions are used to connect and combine the short images.

The output unit 18 outputs the residual image-corrected synthetic image data supplied from the image processor 16. The output unit 18 comprises, for example, a monitor for displaying on the screen a radiographic image, information on the number of times images are taken, and the like; a printer for printing a radiographic image; a memory for storing radiographic image data; an alert sound generator for alerting the radiologist of the imaging timing and the completion of imaging; and the like.

The imaging instruction unit 20 sets an imaging menu (e.g., imaging of the whole lower extremities, imaging of the whole spine, etc.), imaging conditions, an imaging mode, and the like and gives the controller 22 instructions for imaging of the examinee H.

The imaging instruction unit 20 comprises an entry key for setting an imaging menu, imaging conditions, and an imaging mode and instruction means for giving imaging instructions.

The instruction means may be a two-step imaging button. When the 2-step imaging button is depressed to its first step (depressed halfway), the controller 22 causes the imaging unit 12 to stand by for imaging; when the imaging button is depressed to its second step (fully depressed), the controller 22 causes the imaging unit 12 to start imaging.

The system may be adapted to continue to successively take short images (move the radiation detector 42 and the radiation exposure field and effect exposure at given intervals) for long region imaging when the radiologist holds the 2-step imaging button depressed to the second step, and terminate long region imaging when the imaging button held depressed to the second step is released (imaging instruction is terminated).

With such a scheme, when the radiologist makes a judgment that a proper imaging is impossible as in a case, for example, where the examinee H should move involuntarily, the long region imaging can be quickly terminated.

The invention is not limited this way, however. A given number of short images may be automatically taken in response to an instruction to start imaging, with the number of images to be taken and the locations/sizes of the imaging regions preliminarily set and entered.

Further, each time an image is taken (each time exposure is effected), notification thereof may be outputted by way of sound or display on a monitor so that a radiologist who performs imaging may know the imaging (exposure) timing and the number of times imaging has already been performed (the number of images that have already been taken).

The short images P'1 to P'5 may be supplied to the output unit 18 to display a preview of the pre-synthesis images on the monitor. Thus, the preview displayed on the monitor allows the radiologist to know whether images that have so far been taken contain any defect (as in a case, for example, where the examinee H moved so that part of his/her body was out of the imaging range) and stop the long region imaging halfway through the operation by pressing the imaging button when the radiologist actually finds a defect and decides to stop imaging.

The controller 22 controls the imaging system 12, the radiographic data processor 14, the image processor 16, and the output unit 18 according to an imaging instruction signal, etc. supplied from the imaging instruction unit 20.

The controller 22 controls the imaging unit 12, i.e., the exposure field changer 34 and the detector moving mechanism 44, so that imaging is effected according to the imaging menu, the imaging conditions, and the imaging mode as preset.

Further, the controller 22 controls the radiographic data processor 14 so that a radiographic image data of the examinee H, residual image data, and the like are read out from the radiation detector 42 at a given timing.

Further, the controller 22 controls the image processor 16 so that given image processing is performed on radiographic image data supplied from the radiographic data processor 14.

The controller 22 transmits, and controls the transmissions of, information such as information on the imaging mode and information on dark image readout to the residual image correction amount corrector 54 and the residual image corrector 56.

Further, the controller 22 controls the output unit 18 so that a long image supplied from the image processor 16 is displayed on the monitor, printed by the printer and/or stored in the memory.

Figure 5:
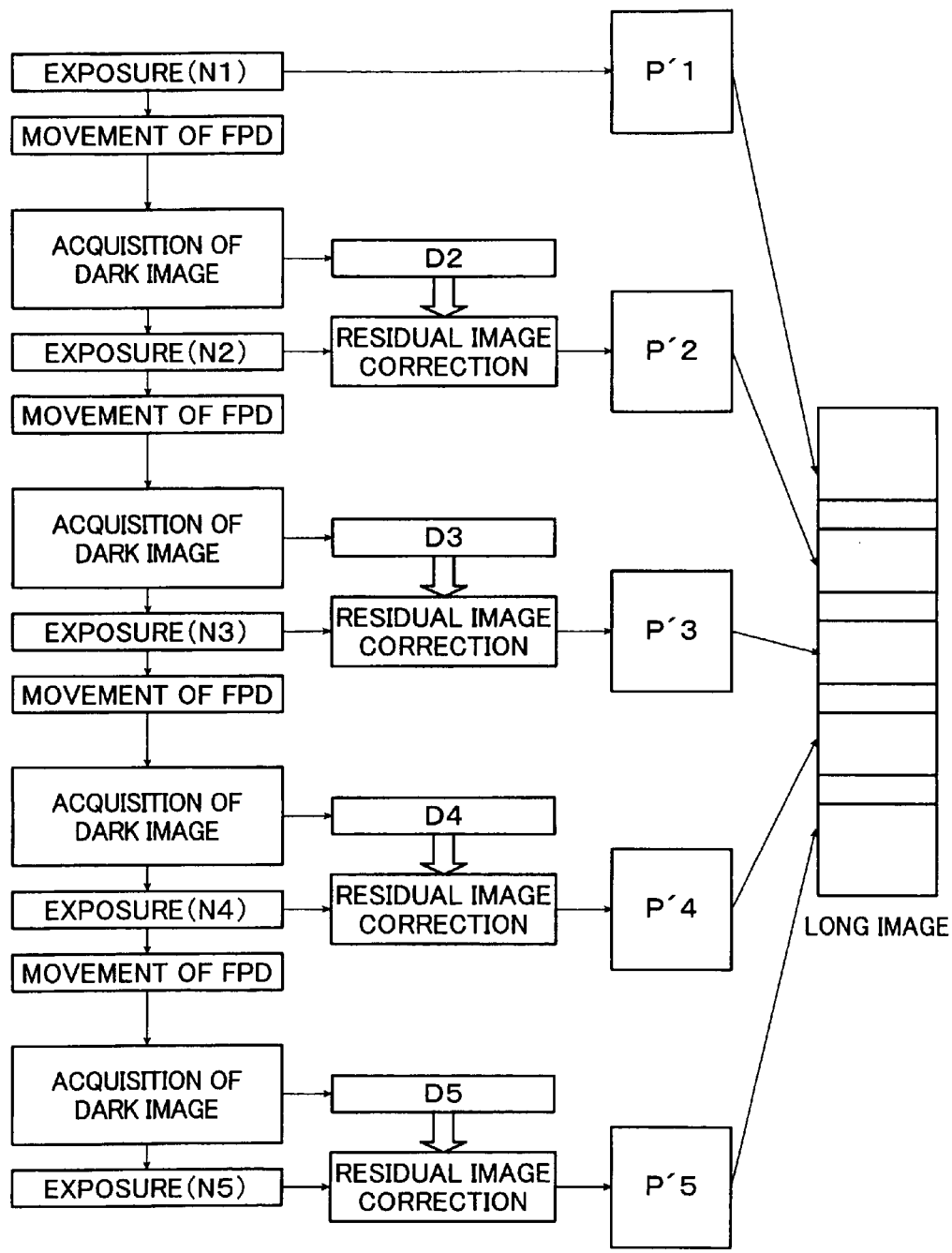
FIG. 5 is a view for explaining the operations whereby a long image is produced by the radiographic imaging system illustrated in FIG. 1.

FIG. 5 is a flow chart for explaining the operations of long region imaging by the radiographic imaging system 10.

In this embodiment, an example of long region imaging will be described wherein the long image mode is selected to take the short images P1 to P5 in the respective imaging positions N1 to N5 schematically illustrated in FIG. 2 and obtain an intended long image from these short images.

First, the radiologist sets an imaging menu (imaging of the whole lower extremities, the whole spine, etc.) and an imaging mode at the imaging instruction unit 20. When the long image mode is set as imaging mode, a long region imaging start position (the first imaging position), e.g., an imaging position N1, is set from the imaging instruction unit 20.

Imaging conditions such as exposure time and irradiation intensity are entered as necessary at the imaging instruction unit 20. The system may have therein set an automatic long image mode in which the system performs automatic setting (or setting is done preliminarily) and a manual long image mode in which the radiologist enters/sets the imaging conditions to permit setting imaging conditions in the long image mode by selecting one of these mode.

When the imaging conditions and the imaging mode are set and the 2-step imaging button is depressed to its first step position at the imaging instruction unit 20, the imaging unit 12 stands by for imaging in response to an instruction from the controller 22.

Specifically, the detector moving mechanism 44 moves the FPD 42 to the first imaging position N1 while the exposure field changer 34 concurrently moves the radiation source 32 to a position where the whole imaging position N1 can be irradiated.

Then, when the imaging button is depressed to its second step, the imaging unit 12 starts the long region imaging.

As illustrated in FIG. 5, a first imaging is performed as the radiation source 32 irradiates the imaging position N1 with radiation (exposes the imaging position N1 to radiation). The emitted radiation penetrates the examinee H and enters the FPD 42. The radiation that has penetrated the examinee H is converted into an electric signal (radiographic image).

When a given radiation accumulation time has passed, the radiographic data processor 14 reads out from the FPD 42 data of a radiographic image that has been taken, thereon performs data processing such as analog-to-digital conversion, and supplies data thus processed to the image processor 16.

In the image processor 16, the image acquirer 48 acquires and transmits radiographic image data supplied from the radiographic data processor 14 to the image corrector 56. This radiographic image, obtained by a first imaging, is transmitted to the image synthesizer 52 as the short image P'1 for the imaging position N1 without residual image correction.

When the first imaging is completed, the detector moving mechanism 44 moves the FPD 42 to the second imaging position N2 while the exposure field changer 34 concurrently moves the radiation source 32 to a position where the whole imaging position N2 can be irradiated. When a given time period has passed after the FPD 42 starts moving, the radiographic data processor 14 reads out from the FPD 42 dark image data of the first radiographic image.

The radiographic data processor 14 performs data processing such as analog-to-digital conversion on the read-out radiographic image data and supplies data thus processed to the image processor 16. In the image processor 16, the image acquirer 48 acquires dark image data supplied from the radiographic data processor 14 and transmits the data to the residual image amount corrector 54.

When the FPD 42 and the radiation source 32 move to the second imaging position N2, the radiographic image P2 starts to be taken. As in the first imaging, the radiation source 32 emits radiation. The emitted radiation penetrates the examinee H and enters the FPD 42. The radiation that has penetrated the examinee H is converted into an electric signal (radiographic image).

When a given radiation accumulation time has passed, the radiographic data processor 14 reads out from the FPD 42 data of the radiographic image P2 taken in the imaging position N2, thereon performs data processing such as analog-to-digital conversion, and supplies data thus processed to the image processor 16.

In the image processor 16, the image acquirer 48 acquires radiographic image data supplied from the radiographic data processor 14 and transmits the data to the residual image corrector 56.

Since the second imaging and the first image are successively performed in a short time period, the radiographic image obtained by the second imaging is affected by the residual image from the first imaging. To remove the effects of the residual image, the dark image data supplied to the residual image amount corrector 54 is used to perform residual image correction.

The residual image amount corrector 54 calculates the correction coefficient $\alpha$ according to the time elapsed from acquisition of dark image data to the time when the radiographic image P2 is taken and multiply the dark image by the correction coefficient $\alpha$ thus worked out to produce residual image data D2, which is transmitted to the residual image corrector 56.

In the residual image corrector 56, the residual image data D2 transmitted from the residual image amount corrector 54 is subtracted from the supplied radiographic image P2 to obtain the corrected short image P'2.

This short image P'2 is transmitted from the residual image corrector 56 to the image synthesizer 52. The short image P'2 is supplied further on to the output unit 18.

Upon completion of the second imaging, the FPD 42 and the radiation source 32 are moved to the third imaging position N3 in the same manner as when the first imaging is completed while the exposure field changer 34 moves the radiation source 32 to a position where the whole imaging position N3 can be irradiated. When a given time period has passed after the FPD 42 starts moving, the radiographic data processor 14 reads out dark image data of the second radiographic image P2 from the FPD 42.

The radiographic data processor 14 performs data processings such as analog-to-digital conversion on the read-out dark image data and supplies data thus processed to the image processor 16. In the image processor 16, the image acquirer 48 acquires dark image data supplied from the radiographic data processor 14 and transmits the data to the residual image amount corrector 54 of the image corrector 50. The residual image amount corrector 54 multiplies the dark image data by the correction coefficient $\alpha$ to produce residual image data D3 and transmits the data D3 to the residual image corrector 56.

When the FPD 42 and the radiation source 32 move to the third imaging position N3, the radiographic image P3 starts to be taken. In the imaging unit 12, the FPD 42 converts the radiation emitted from the radiation source 32 and having penetrated the examinee H into an electric signal (radiographic image), as when taking the radiographic image P2. The radiographic data processor 14 reads out data of the radiographic image P3 from the FPD 42, thereon performs data processing such as analog-to-digital conversion, and supplies data thus processed to the image processor 16. In the image processor 16, the image acquirer 48 acquires data of the radiographic image P3 supplied from the radiographic data processor 14 and transmits the data to the residual image corrector 56 of the image corrector 50. In the residual image corrector 56, the residual image data D3 is subtracted from the radiographic image P3 to obtain the corrected short image P'3 for the imaging position N3. The short image P'3 thus produced is transmitted to the image synthesizer 52.

Likewise, fourth and fifth radiographic images P4 and P5 are taken and dark images are acquired, and the corrected short images P'4 and P'5 are sequentially produced based upon residual image data D4 and D5 and transmitted to the image synthesizer 52.

Upon completion of the fifth imaging, the image synthesizer 52 combines the corrected short images P'1 to P'5 to produce a long radiographic image.

The long image thus produced is supplied to the output unit 18. In the output unit 18, the long image supplied from the image synthesizer 52 is, for example, displayed on the monitor, printed by the printer and/or stored in the memory.

The short images P'1 to P'5 may be displayed on the monitor of the output unit 18 for preview.

In a typical long region imaging, short images are successively taken in a short period of time such that a residual image remaining from the previous short image greatly affects the next short image. According to this embodiment, however, a dark image is acquired before taking a short image, and dark image data (dark image correction data) is produced from the dark image and used to perform dark image correction. Thus, adverse effects of a residual image from the previous short image upon the short image to be subsequently taken can be eliminated, producing a high quality image free from image degradation due to residual image in a long region imaging wherein a long image of, for example, the whole lower extremities or the whole spine is taken.

Note that normal imaging by the imaging system 10 of the invention may be performed in the same manner as by known radiographic imaging systems. Further, the imaging system 10 may be adapted to perform residual image correction also in normal imaging where required.

In the above embodiment, the FPD 42 acquires a dark image when a given time has elapsed after the radiation source 32 starts moving after effecting the first exposure in the first imaging position N1 and before reaching the second imaging position N2 (while the FPD 42 is moving). However, the FPD 42 may be adapted to acquire a dark image after the radiation source 32 stops in the second imaging position N2 and before the radiation source 32 effects the second exposure (when the FPD 42 is stationary before imaging starts).

However, when the FPD 42 acquires a dark image before the radiation source 32 reaches the second imaging position N2 as in the above embodiment, the need to specifically provide time to acquire a dark image is eliminated. Accordingly, images can be taken in a reduced time period, a burden on the examinee H can be reduced, and troubles such as an inadvertent movement of the examinee H during long region imaging can be minimized.

On the other hand, in the scheme wherein a dark image is acquired after the FPD 42 reaches the second imaging position N2, processing such as acquisition of a dark image is done between the time when the FPD 42 stops and the time when a short image is taken, which elongates the time it takes for long region imaging.

In return, in the scheme wherein a dark image is acquired after the FPD 42 reaches the second imaging position N2, the time that elapses from the acquisition of a dark image until the time when a short image is taken (exposure is effected) can be reduced, and therefore the accuracy of residual image correction can be increased, thus producing a long image having a higher quality.

Whether a dark image should be acquired when the FPD 42 is moving or when the FPD 42 is stationary and before the next short image is taken may be determined as appropriate according to such factors as image quality and productivity (processing capabilities) required of the imaging system.

Alternatively, acquisition of a dark image accomplished when the FPD 42 is moving and acquisition of a dark image accomplished when the FPD 42 is stationary and before the next short image is taken may be preliminarily set as modes in the imaging system 10 to allow selection of an alternative by selection of a mode.

Where acquisition of a dark image is accomplished when the FPD 42 is stationary and before a short image is taken, residual image amount correction may be dispensed with or an option to select between performing residual image amount correction and not performing residual amount image correction may be provided. Where acquisition of a dark image is accomplished when the FPD 42 is being moved, residual image amount correction is preferably performed but the invention is not limited this way; residual image amount correction may be dispensed with or an option to select between performing residual image amount correction and not performing residual image amount correction may be provided.

In the above embodiment, the radiographic imaging system is described as it is used for imaging in the standing position wherein the examinee H stands for imaging. However, the invention is not limited this way and may be applied to known radiographic imaging systems used for imaging in the lying position wherein the examinee H lies for imaging.

In the above embodiment, the radiation exposure field is changed in the long region imaging by moving the radiation source 32 in a given direction (body axis direction), but the invention is not limited this way and permits use of various known means of changing the radiation exposure field.

An example thereof is a method whereby the radiation exposure field is changed by varying the angle of the radiation source (by turning the tube). Alternatively, one may use a method using a tube capable of irradiating the whole region to be covered by the long region imaging and an aperture for restricting the exposure field of the radiation emitted from the radiation source. By that method, the aperture is moved in a given direction (body axis direction) to change the radiation exposure field.

The above embodiment has a configuration comprising means for changing the radiation exposure field but the invention is not limited this way and permits use of a configuration without means for changing the radiation exposure field. For example, the configuration may comprise a radiation source capable of irradiating the whole region to be covered by the long region imaging to perform long region imaging just by moving the radiation detector to imaging positions.

While the radiographic imaging method of the invention has been in detail, the above embodiment is only illustrative of the invention, and it is to be understood that various changes and modifications may be made without departing from the spirit of the invention.

What is claimed is:

1. A radiographic imaging system for acquiring a long radiographic image by combining short images taken in a plurality of imaging positions, the system comprising:

imaging means including a radiation source for emitting radiation and a radiation detector for detecting radiation emitted from the radiation source and having penetrated a subject;

moving means for moving the imaging means between a plurality of imaging positions that partially share an imaging region with each other;

control means for sequentially moving the imaging means to the imaging positions with the moving means, causing the radiation source to emit radiation to acquire a short image with the radiation detector in each of the imaging positions, and acquiring a dark image with the radiation detector after acquiring the short image without emitting radiation from the radiation source; and image processing means for combining corrected short images to obtain a long radiographic image after performing residual image correction upon the short image acquired in each of the imaging positions based upon the dark image acquired immediately before the acquisition of the short image to prevent deterioration of image quality, due to residual image remaining, from occurring.

2. The radiographic imaging system according to claim 1, wherein the imaging positions are located in such a manner that part of the imaging region covered by the imaging means is shared by the imaging positions.

3. The radiographic imaging system according to claim 1, wherein the control means acquires the dark image with the radiation detector during the moving of the imaging means by the moving means toward the next imaging position after the short image is acquired in each of the imaging positions.

4. The radiographic imaging system according to claim 1, wherein the control means acquires the dark image with the radiation detector after the moving of the imaging means by the moving means to the next imaging position is completed and before the short image is acquired in the next imaging position.

5. The radiographic imaging system according to claim 1, wherein the image processing means does not perform residual image correction on the short image acquired in a first imaging position in the plurality of imaging positions and treats that short image as corrected short image.

6. The radiographic imaging system according to claim 1, wherein the control means acquires a first short image after acquiring a dark image in a first imaging position in the plurality of imaging positions.

* * * * *